(12) United States Patent
Ishay et al.

(10) Patent No.: US 7,904,143 B2
(45) Date of Patent: Mar. 8, 2011

(54) BINARY LOGISTIC MIXED MODEL FOR COMPLEX FRACTIONATED ATRIAL ELECTROGRAM PROCEDURES

(75) Inventors: Eva Ishay, Haifa (IL); Gal Hayam, Tivon (IL); Tsahi Grinberg, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 402 days.

(21) Appl. No.: 12/168,581

(22) Filed: Jul. 7, 2008

(65) Prior Publication Data
US 2010/0004550 A1    Jan. 7, 2010

(51) Int. Cl.
*A61B 5/046* (2006.01)
(52) U.S. Cl. .......... 600/518; 600/515; 607/101; 128/923
(58) Field of Classification Search ........................ None
See application file for complete search history.

(56) References Cited

U.S. PATENT DOCUMENTS

| | | | |
|---|---|---|---|
| 5,546,951 A | 8/1996 | Ben-Haim | |
| 5,738,096 A | 4/1998 | Ben-Haim | |
| 6,226,542 B1 | 5/2001 | Reisfeld | |
| 6,301,496 B1 | 10/2001 | Reisfeld | |
| 6,332,089 B1 | 12/2001 | Acker et al. | |
| 6,618,612 B1 | 9/2003 | Acker et al. | |
| 6,669,692 B1 | 12/2003 | Nelson et al. | |
| 6,690,963 B2 | 2/2004 | Ben-Haim et al. | |
| 6,892,091 B1 | 5/2005 | Ben-Haim et al. | |
| 2004/0068178 A1 | 4/2004 | Govari | |
| 2004/0102769 A1 | 5/2004 | Schwartz et al. | |
| 2004/0147920 A1 | 7/2004 | Keidar | |
| 2006/0122526 A1* | 6/2006 | Berenfeld et al. | 600/515 |
| 2007/0197929 A1* | 8/2007 | Porath et al. | 600/523 |
| 2008/0188765 A1* | 8/2008 | Stolarski et al. | 600/518 |

FOREIGN PATENT DOCUMENTS
WO    WO 96/05768 A1    2/1996

OTHER PUBLICATIONS

Nademanee, K et al. A New Approach for Catheter Ablation of Atrial Fibrillation: Mapping of the Electrophysiologic Substrate, J. Am. Coll. Cardiol. 2004;43;2044-2053.

* cited by examiner

*Primary Examiner* — Kennedy J Schaetzle
(74) *Attorney, Agent, or Firm* — Louis J. Capezzuto (57) ABSTRACT

Methods and systems are provided for locating arrhythmogenic cardiac focus. A training set of electrical signal data is acquired and automatically analyzed to identify CFAE locations. The data representing the CFAE locations are and subjected to determinations of medical significance, such as ablation decisions, by a battery of physicians. The decisions and descriptive statistics of the data are fitted to a binary logistic mixed model, in which the physician decisions are treated as random effects. The model is then applied to patient CFAE data to establish estimates of medical significance, such as suitability for ablation.

10 Claims, 6 Drawing Sheets

BINARY LOGISTIC MIXED MODEL FOR COMPLEX FRACTIONATED ATRIAL ELECTROGRAM PROCEDURES

BACKGROUND OF THE INVENTION

1. Field of the Invention

This invention relates to the diagnosis and treatment of cardiac arrhythmias. More particularly, this invention relates to obtaining information indicative of regional electrical activity in the cardiac chambers, and to the identification and treatment of arrhythmogenic areas.

2. Description of the Related Art

The meanings of certain acronyms and abbreviations used herein are given in Table 1.

TABLE 1

| Acronyms and Abbreviations | |
|---|---|
| CFAE | Complex Fractionated Atrial Electrogram |
| RMS | Residual Mean Square |
| CV | Coefficient of Variation |
| SD | Standard Deviation |

Cardiac arrhythmias such as atrial fibrillation are an important cause of morbidity and death. Commonly assigned U.S. Pat. No. 5,546,951, and U.S. Pat. No. 6,690,963, both issued to Ben Haim; and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. No. 6,226,542, and U.S. Pat. No. 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity at multiple points in the heart chamber.

Over the past decade, several mapping studies in human atrial fibrillation have made the following important observations. Atrial electrograms during sustained atrial fibrillation have three distinct patterns: single potential, double potential and a complex fractionated atrial electrograms (CFAE's). The CFAE areas represent the atrial fibrillation substrate sites and become important target sites for ablation. By ablating areas having persistent CFAE's, atrial fibrillation may be eliminated and even rendered non-inducible.

In the document *A New Approach for Catheter Ablation of Atrial Fibrillation: Mapping of the Electrophysiologic Substrate*, Nademanee et al., J. Am. Coll. Cardiol., 2004; 43(11): 2044-2053, it is proposed that atrial fibrillation may be successfully treated by ablating sites exhibiting a complex fractionated atrial electrogram. The authors identified areas of CFAE during atrial fibrillation, and then applied radiofrequency ablation to these areas. As a result of the ablation, the atrial fibrillation was resolved in the large majority of the cases.

SUMMARY OF THE INVENTION

Copending commonly assigned U.S. patent application Ser. No. 11/620,370, entitled "Mapping of Complex Fractionated Atrial Electrogram", which is herein incorporated by reference, discloses the automatic detection and mapping of areas within cardiac chambers exhibiting complex fractionated electrograms. Electrogram signals are analyzed to count the number of complexes whose amplitude and peak-to-peak intervals meet certain criteria of magnitude and frequency.

According to an aspect of the invention, various descriptive statistics, e.g., standard deviation, mean, range, are used to describe the basic features of data obtained in a patient session. They provide simple summaries about the sample and the measures. Such statistics are incorporated in graphic displays, and provide a basis for quantitative analysis of the data.

In another aspect of the invention, inferential statistics are used to make estimates about the population of CFAE location data or to make judgments of the probability that an observed difference between groups of physician operators is significant or may have happened by chance. A model employing the inferential statistics predicts a per-point likelihood of suitability for ablation.

An embodiment of the invention provides a method for locating an arrhythmogenic focus in a heart of a living subject, which is carried out by obtaining training electrical signal data from respective training locations of a training set of hearts, automatically analyzing the training data to identify training complex fractionated electrograms therein, recording ablation decisions of a plurality of observers with respect to the training complex fractionated electrograms, generating first estimations of medical significance, e.g., suitability for ablation at the respective training locations by fitting a mixed regression model to the training complex fractionated electrograms and the ablation decisions. The method is further carried out by obtaining patient electrical signal data from respective locations of a patient heart, automatically analyzing the patient electrical signal data to identify patient complex fractionated electrograms in the patient heart, applying the mixed regression model to the patient complex fractionated electrograms to obtain second estimations of medical significance at the respective locations of the patient heart, and displaying an indication that one or more of the respective locations of the patient heart are medically significant.

According to an aspect of the method, the mixed regression model is a binary logistic mixed model having fixed effects comprising the coefficient of variation and range of the training electrical signal data, and having random effects comprising the first estimations of suitability for ablation.

According to an aspect of the method, the observers comprise five observers.

According to a further aspect of the method, the ablation decisions comprise first decisions to ablate primary ablation locations selected from the respective training locations and second decisions to ablate secondary ablation locations selected from the respective training locations.

Other embodiments of the invention provide computer software product and apparatus for carrying out the above-described method.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client/server environment, such software programming code may be stored on a client or a server. The software programming code may be embodied on any of a variety of known tangible media for use with a data processing system, such as a diskette, hard drive, or CD-ROM. The code may be distributed on such media, or may be distributed to users from the memory or storage of one computer system over a network of some type to storage devices on other computer systems for use by users of such other systems.

Overview

The above-noted U.S. patent application Ser. No. 11/620,370 discloses the use of an intracardiac probe to obtain signal data from a plurality of contact points on a cardiac chamber's endocardial surface. The data is automatically analyzed to identify voltage peaks having amplitudes within a predefined voltage range, and to identify peak-to-peak intervals between the identified voltage peaks that occur within a predefined time range. Confidence levels are determined as a function of a number of peak-to-peak intervals intervening between successive complex fractionated electrograms. Functional maps indicating average complex interval, shortest complex interval, and confidence levels may be produced for display.

It has been found that reliable recommendations for diagnostic and therapeutic intervention, e.g., ablation of candidate CFAE sites, can be obtained by construction of a mixed regression model of intracardiac signal data taken from presumptive CFAE sites, in which the per point binary ablation decisions of a group of physicians were treated as a random effect. In the current embodiments a binary logistic mixed model is used. Based on the standard deviation, absolute mean and range of the amplitude of a signal taken from a point, the model predicts the probability that a physician belonging to the group from which the model was derived would make a positive decision regarding the significance of that point. The model may be applied to data obtained from new patient studies, and a screen display generated to inform the operator of significance of the data, for example, the likelihood of a positive ablation decision by the group at any given point.

System Architecture

Figure 1:
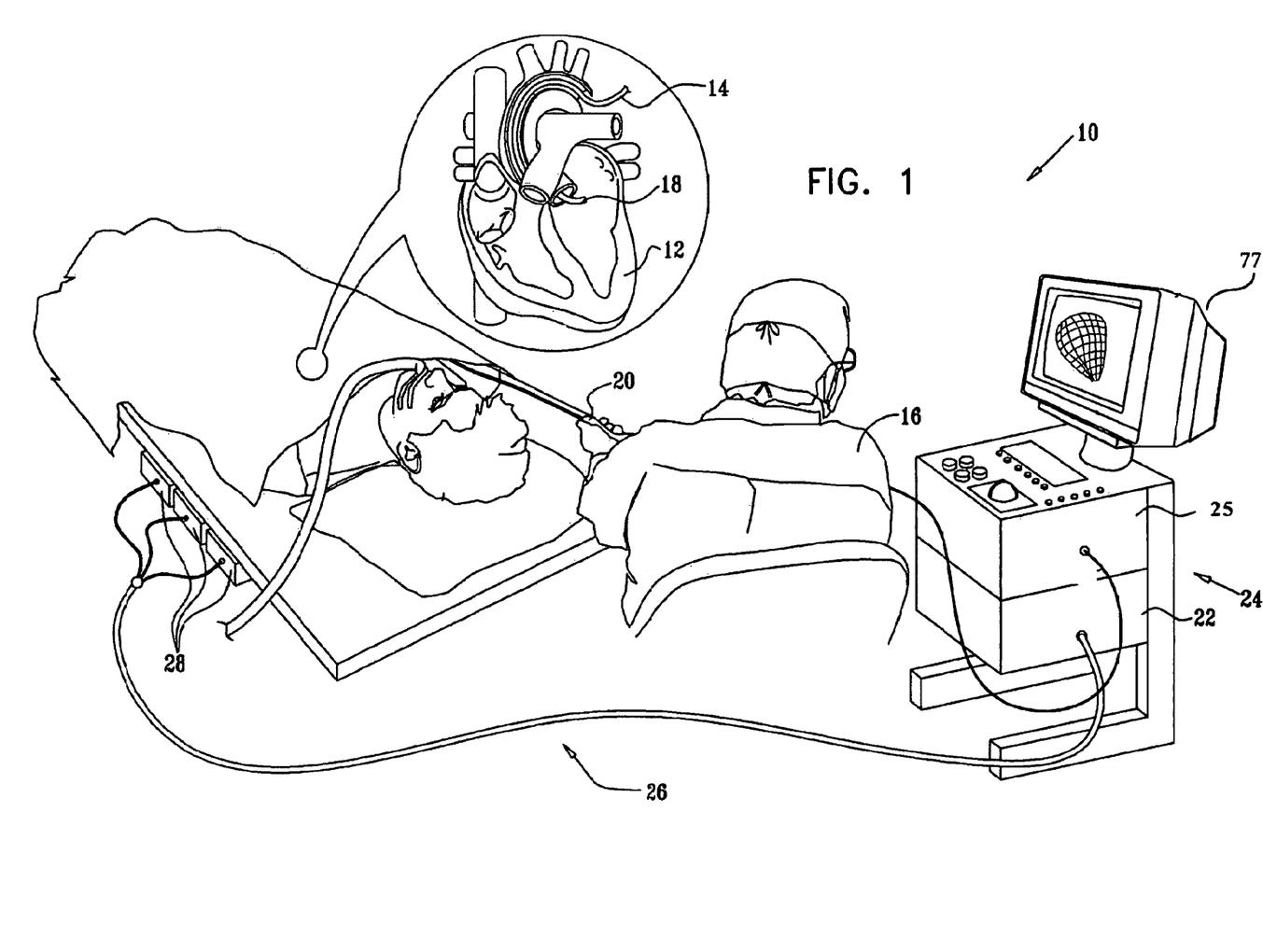
FIG. 1 is a pictorial illustration of a system for detecting areas of abnormal electrical activity and performing ablative procedures on a heart of a living subject in accordance with a disclosed embodiment of the invention.

Turning now to the drawings, reference is initially made to FIG. 1, which is a pictorial illustration of a system 10 for detecting areas of abnormal electrical activity and performing ablative procedures on a heart 12 of a living subject 21 in accordance with a disclosed embodiment of the invention. The system comprises a probe, typically a catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Electrical activation maps are then prepared, according to the methods disclosed in the above-noted U.S. Pat. Nos. 6,226,542, and 6,301,496, and in commonly assigned U.S. Pat. No. 6,892,091, whose disclosure is herein incorporated by reference.

Areas determined to be abnormal by evaluation of the electrical activation maps can be ablated using application of thermal energy, e.g., by passage of radiofrequency electrical current through wires in the catheter to one or more electrodes at the distal tip 18, which apply radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/

0102769, whose disclosure is herein incorporated by reference. The principles of the invention are disclosed with respect to atrial complex fractionated electrograms, but can be applied to all heart chambers, to epicardial as well as endocardial approaches, and to mapping in sinus rhythm, and when many different cardiac arrhythmias are present.

The catheter 14 typically comprises a handle 20, having suitable controls on the handle to enable the operator 16 to steer, position and orient the distal end of the catheter as desired to the ablation. To aid the operator 16, the distal portion of the catheter 14 contains position sensors (not shown) that provide signals to a positioning processor 22, located in a console 24. The catheter 14, may be adapted, mutatis mutandis, from the ablation catheter described in commonly assigned U.S. Pat. No. 6,669,692, whose disclosure is herein incorporated by reference. The console 24 typically contains an ablation power generator 25 and a display monitor 77 on which indications of suitability for ablation may be displayed.

The positioning processor 22 is an element of a positioning subsystem 26 that measures location and orientation coordinates of the catheter 14. Throughout this patent application, the term "location" refers to the spatial coordinates of the catheter, and the term "orientation" refers to its angular coordinates. The term "position" refers to the full positional information of the catheter, comprising both location and orientation coordinates.

In one embodiment, the positioning subsystem 26 comprises a magnetic position tracking system that determines the position and orientation of the catheter 14. The positioning subsystem 26 generates magnetic fields in a predefined working volume its vicinity and senses these fields at the catheter. The positioning subsystem 26 typically comprises a set of external radiators, such as field generating coils 28, which are located in fixed, known positions external to the patient. The coils 28 generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking systems that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning subsystem 26 shown in FIG. 1 uses magnetic fields, the methods described below may be implemented using any other suitable positioning subsystem, such as systems based on electromagnetic fields, acoustic or ultrasonic measurements.

Figure 2:
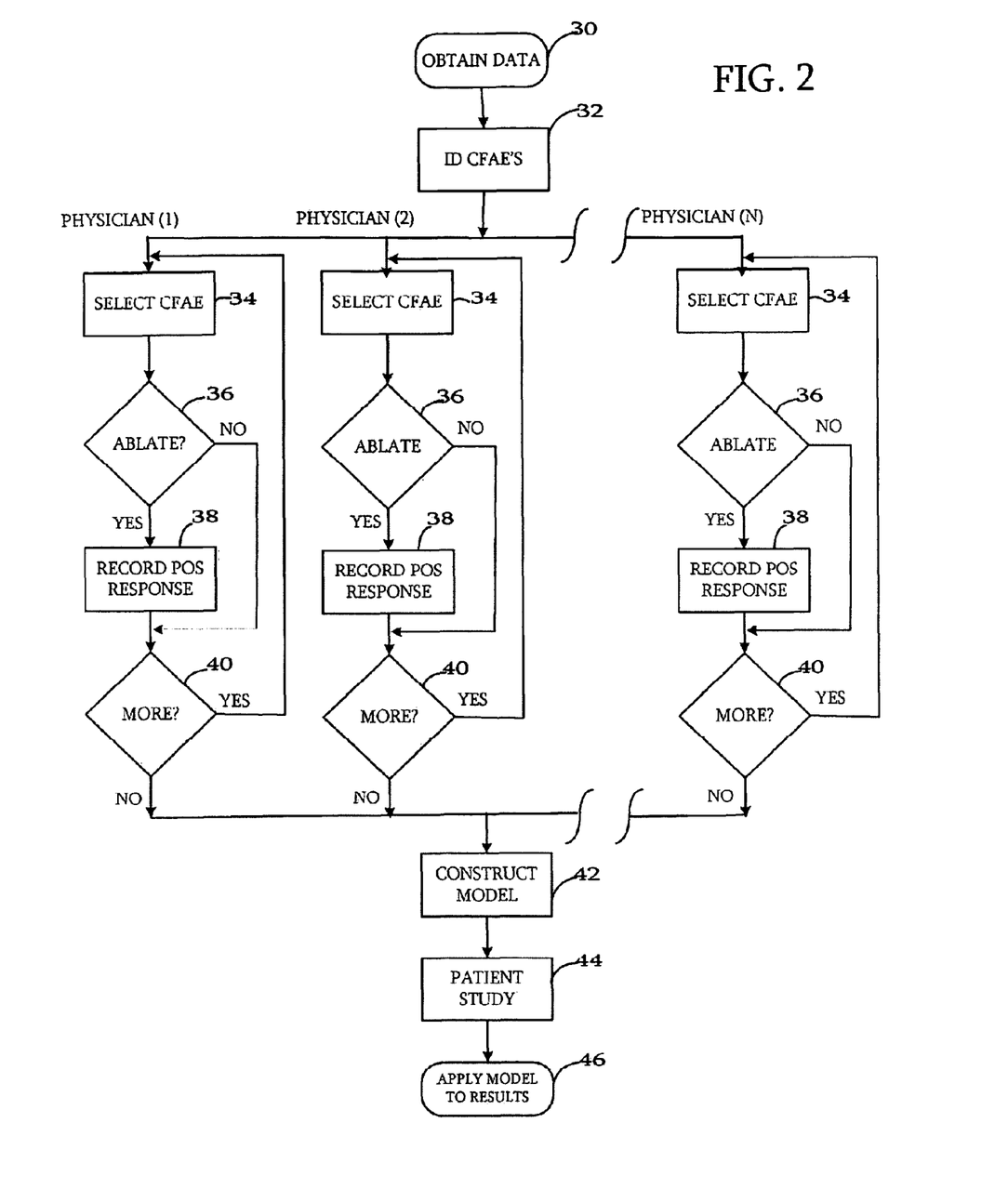
FIG. 2 is a flow chart of a method of constructing a binary logistic mixed model for evaluation of electroanatomic data taken from the heart in accordance with a disclosed embodiment of the invention.

Reference is now made to FIG. 2, which is a flow chart of a method of constructing a binary logistic mixed model for evaluation of electroanatomic data taken from the heart in accordance with a disclosed embodiment of the invention.

At initial step 30 a training set of data is acquired by subjecting a set of patients to cardiac catheterization during which a probe signals are acquired from multiple points on the endocardium of each patient. The set may comprise only one patient. Alternatively, the set may comprise a plurality of patients. The procedure described in the above-noted U.S. patent application Ser. No. 11/620,370 is suitable, using the system 10 (FIG. 1). The system 10 can be realized as the CARTO XP EP Navigation and Ablation System, available from Biosense Webster, Inc., 3333 Diamond Canyon Road, Diamond Bar, Calif. 91765, suitably modified to execute the procedures described herein. Essentially, a probe typically having at least one mapping electrode and a plurality of non-contact electrodes is advanced over a plurality of contact points on the cardiac chamber's endocardial surface. Location and electrical information is acquired while the contact electrode is in contact with each of the contact points. Typically, the above-described contacting and information acquisition steps are effected at between 5-15 such contact points. Since there are multiple non-contact electrodes 38, the total number of points used to acquire data in a chamber may be 160 points or more. The resultant location and electrical information acquired from the electrode 32 and the non-contact electrodes 38 at each of acquisition step provides the basis for generating an electrical map of the heart chamber and a binary logistic mixed model.

Next, at step 32 data obtained in initial step 30 that meet criteria for complex fractionated electrograms are automatically identified as candidate CFAE locations. This is a capability provided by the above-noted CARTO XP EP Navigation and Ablation System. Complex fractionated electrograms are nominally defined as areas that exhibit one of the following characteristics. In practice, a user or operator may vary these characteristics, according to his experience and judgment with respect to a particular patient:

(1) areas of the atrium that have fractionated electrograms composed of two deflections or more and/or perturbation of the baseline with a continuous deflection of a prolonged activation complex over a 10-sec recording period; or (2) areas of the atrium where the electrogram has a very short cycle length (e.g., 120 ms) averaged over a 10 second recording period. The recording period is not critical, and recording intervals of other lengths may be used.

The number of intervals between complexes may also be represented. In a current embodiment the following thresholds and parameters are used:

0.05__0.15__50__110—voltage range of 0.05-0.15 mV, and cycle length of 50-110 ms 0.05__0.15__60__120—voltage range of 0.05-0.15 mV, and cycle length of 60-120 ms.

In the following discussion, evaluation of CFAE locations from the standpoint of suitability for ablation is presented by way of example. However, other diagnostic and therapeutic purposes can be made from evaluation of the CFAE locations, as will occur to medical practitioners. The techniques may be readily adjusted to such purpose by evaluating the CFAE locations from the standpoint of medical significance such as conforms to the requirements of a particular diagnostic or therapeutic purpose.

In the following sequences, the data resulting from step 32 is submitted to a battery of physicians (shown in FIG. 2 as physician 1-physician N) for evaluation. These physicians have expertise in the field of cardiology. However, they may not use identical criteria for determining that a candidate CFAE location identified in step 32 is suitable for ablation. The physicians each make binary ablation decisions for each identified CFAE complex. The binary logistic mixed model that is derived from the data and the ablation decisions incorporates the collective knowledge and judgment of the battery of physicians. It is recommended that at least five physicians participate in the evaluation process. If too small a number is used, then the model may have limited value, as sufficient diversity of opinion and judgment will not be available. It is desirable that the battery of physicians perform their respective evaluations individually, without mutual interactions in order to avoid inadvertently biasing the results.

At step 34 a CFAE is selected. A display, which may include graphical and tabular information regarding the current CFAE is typically presented to the evaluating physician. This display generally provides a visual trace of the CFAE complexes, and shows such characteristics as peak height, duration, intervals between complexes, and confidence level. The confidence level is an indication of the number of CFAE complexes observed during a monitoring interval.

Control now proceeds to decision step 36, where it is determined by the physician if the location represented by the current CFAE is suitable for ablation. If the determination at decision step 36 is affirmative, then control proceeds to step 38. A positive response is recorded.

If the determination at decision step 36 is negative a negative response is inferred. In either case, control proceeds to decision step 40, where it is determined if more CFAEs remain to be evaluated. If the determination at decision step 40 is affirmative, then control returns to step 34.

If the determination at decision step 40 is negative, then following completion of decision step 40 by all of the physicians in the battery, control proceeds to step 42. A binary logistic mixed model is constructed based on the data and the binary ablation decisional responses of the physician. This results in respective likelihood estimations of suitability for ablation at the CFAE locations. Details of the binary logistic mixed model are presented below.

Next, at step 44 a patient examination is conducted by repeating the performance of initial step 30 and step 32 on a subject.

At final step 46, the binary logistic mixed model constructed in step 42 is applied to the data obtained from the patient examination, and the per-CFAE likelihood estimates of suitability for ablation is displayed for the operator. The operator may be rely on or be assisted by the display in making determinations to ablate particular CFAE locations. Locations in the patient that are identified as having a sufficient likelihood of ablation success may then be ablated.

Binary Logistic Mixed Model

The following basic statistics are used in the construction of the binary logistic mixed model.

Let $X_i$—the amplitude of a signal at time i, i=1, . . . , n.
Then the standard deviation is given by.

$$SD \sqrt{\frac{\sum_{i=1}^{n}(x_i - \bar{x})^2}{n-1}}, \qquad (1)$$

when $$\bar{x} = \frac{\sum_{i=1}^{n} x_i}{n}.$$

The coefficient of variation is:

$$CV = \frac{SD}{\bar{x}}, \qquad (2)$$

and $$Range = X_{max} - X_{min} |. \qquad (3)$$

In the binary logistic mixed model, because each physician operates according to his own experience, a physician constitutes a random effect. The statistics SD, CV, and Range of the signals are treated as fixed effects.

The term $Y_{ik}$ indicates the ordinary response of the $k^{th}$ Physician at the $i^{th}$ CFAE in decision step 36 (FIG. 2). Then in a category j, the probability of a positive response (decision to ablate) in decision step 36 is given by:

$$p_j = P(Y_{ik} = j | z_{ik}, s_k) \qquad (4)$$

where $Z_{ik}$ are covariates at the $k^{th}$ Physician at the $i^{th}$ CFAE, and $s_k$ is a random physician effect. Then $$Q_j = P(Y_{ik} \leq j) = p_1 + p_2 + \ldots + p_j \Rightarrow p_1 = Q_1, \; p_2 = Q_2 - Q_1, \ldots, p_J = 1 - Q_{J-1}, (j=1, \ldots, J-1), \qquad (5)$$

When j=2, $Y_{ik}$ indicates the binary response. Proportional Odds are:

$$logit(Q_j) \equiv \log\left(\frac{Q_j}{1-Q_j}\right) = \alpha_j + z_{ik}^T \underline{\beta} + s_k, \qquad (6)$$

$(j = 1, \ldots, J-1),$ and $$s_k \sim N(0, \sigma_s^2) \qquad (7)$$

$$P(\underline{Y}_k = \underline{y}_k | z_{ik}, s_k) = \prod_i \prod_j p_j^{n_{kij}}, \qquad (8)$$

where $n_{kij}=1$ if a response equals category j for physician k at point I, and $n_{kij}=0$ otherwise.

Likelihoods are calculated as follows:

$$l(\underline{\alpha}, \underline{\beta}, \delta) = \prod_k \int_{s_k} \prod_i \prod_j p_j^{n_{kij}} q(s_k) ds_k, \qquad (9)$$

where $\alpha_j$ is the $j^{th}$ cut point or intercept parameter, and $\beta$ is a vector of the slope parameters. q(s) is a normal density function with 0 mean and variance $\sigma_s^2$.

The model is fitted by a method of maximum likelihood, based on directly maximizing an approximate integrated likelihood. This can be done using the NLMIXED procedure in the program SAS/STAT®, available from SAS Institute Inc., 100 SAS Campus Drive, Cary, N.C. 27513-2414.

Alternative Embodiment 1

Figure 3:
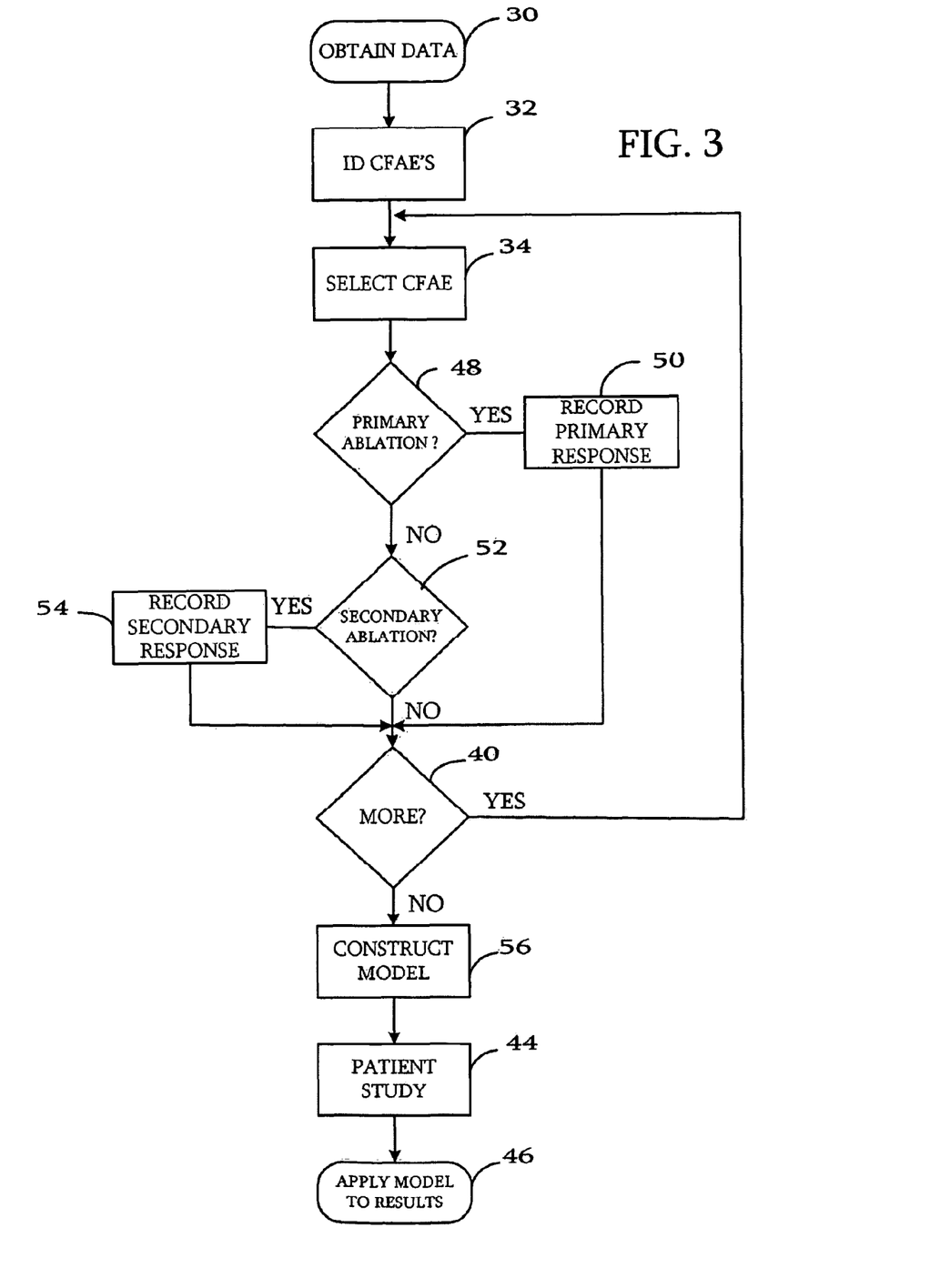
FIG. 3 is a flow chart of a method of constructing a binary logistic mixed model in accordance with an alternate embodiment of the invention.

Reference is now made to FIG. 3, which is a flow chart of a method of constructing a generalization of a binary logistic mixed model, known as an ordinal logistic mixed model, in accordance with an alternate embodiment of the invention. The method is similar to that described with reference to FIG. 2, except now the battery of physicians are instructed to discriminate between primary ablation points, in which the physician is highly confident that ablation will be effective, and secondary ablation points, which are suitable for ablation, but for which physician confidence in predicting a successful result is less. A third group comprises points that the physician considers to be unsuitable for ablation. These classifications are necessarily subjective, but nevertheless result in a practical gradation of classification of points by likelihood of ablation success.

For clarity of presentation, a sequence is shown in FIG. 3 only for one physician, it being understood that evaluation of the CFAE's is to be performed by a battery of physicians as shown in FIG. 2. Details of steps that are identical to those of FIG. 2 are generally not repeated.

After selection of a CFAE location in step 34, control proceeds to decision step 48, where it is determined if the current CFAE is significant for a particular medical purpose, e.g., a primary ablation point. If the determination at decision step 48 is affirmative, then control proceeds to step 50. A primary response is recorded. Control then proceeds to decision step 40.

If the determination at decision step 48 is negative, it is still possible that ablation might be performed. Control proceeds to decision step 52, where it is determined if the current CFAE is a secondary ablation point. If the determination at decision step 52 is affirmative, then control proceeds to step 54. A secondary response is recorded. Control then proceeds to decision step 40.

If the determination at decision step 40 is affirmative, then control returns to step 34.

If the determination at decision step 40 is negative, then control proceeds to step 56, which a logistic mixed model is constructed. A tabular display may be produced. Additionally or alternatively, a composite graphical display may be produced.

Example 1

In this Example, a training set was evaluated, using the procedure described in FIG. 3.

Figure 4:
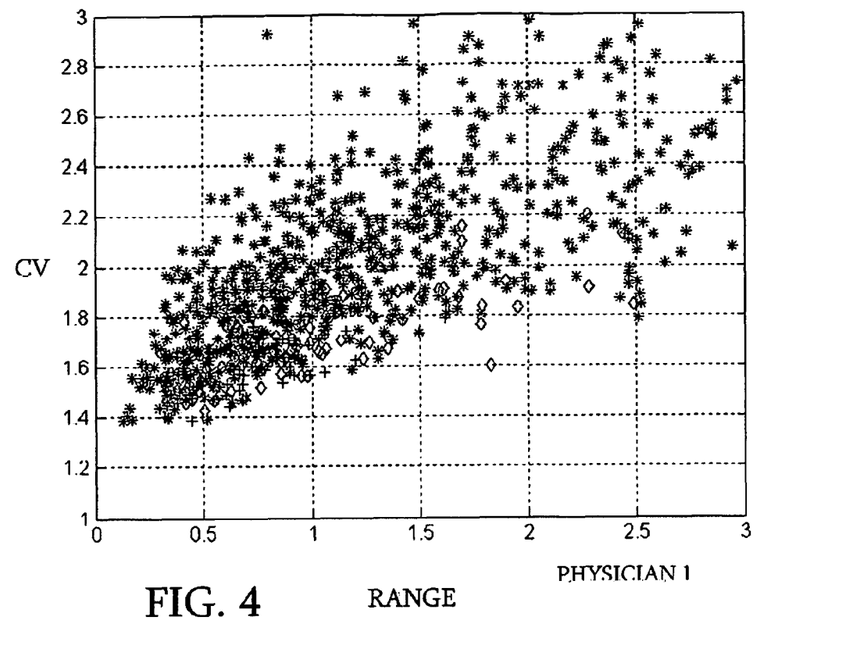
FIG. 4 is a scattergraph generated using the method shown in FIG. 3, illustrating binary responses of one observer in a training set, in accordance with a disclosed embodiment of the invention.

The training set comprised 920 CFAE locations, obtained from 10 patient studies and was submitted to a battery of five physicians. Reference is now made to FIG. 4, which is a scattergram generated in step 56 (FIG. 3) illustrating binary responses of one observer in accordance with a disclosed embodiment of the invention. FIG. 4 shows CFAE's detected in the training set, indicating decisions made by Physician No. 1. The range of the CV of the signal at each CFAE location is plotted against its range. "+" symbols indicate physician decisions to designate CFAE locations as primary ablation locations. Diamond-shaped symbols ("◊") indicate secondary ablation locations. "*" symbols indicate decisions not to ablate. Physician No. 1 represents an extreme among the group, in that he is relatively likely to designate points for primary ablation.

Figure 5:
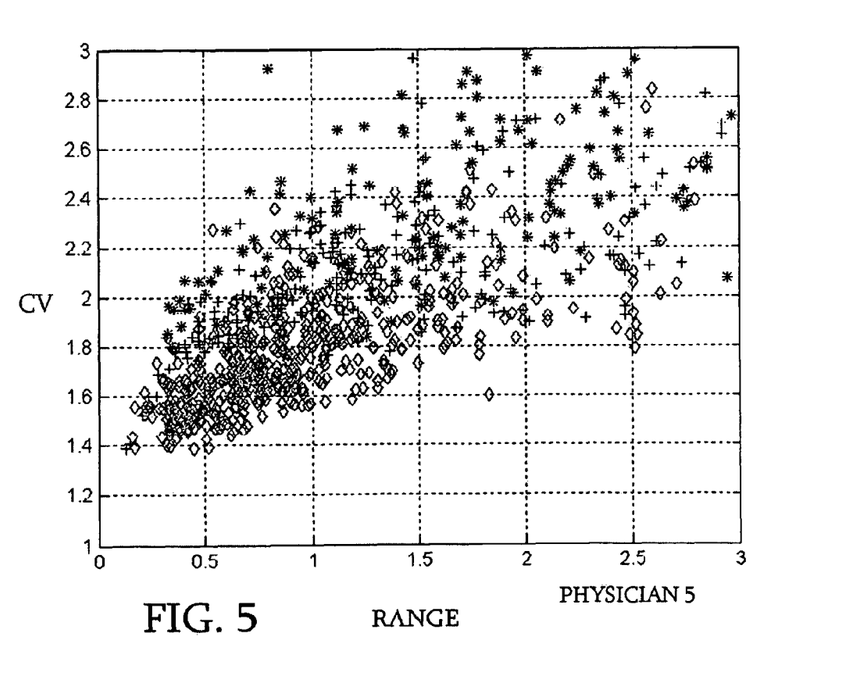
FIG. 5 is a scattergraph generated using the method shown in FIG. 3, illustrating binary responses of another observer in a training set, in accordance with a disclosed embodiment of the invention.

Reference is now made to FIG. 5, which is a scattergram similar to FIG. 4, but which applies to Physician No. 5. Physician No. 5 is at another extreme within the battery of physicians, in that he is relatively unlikely to designate points for primary ablation.

Figure 6:
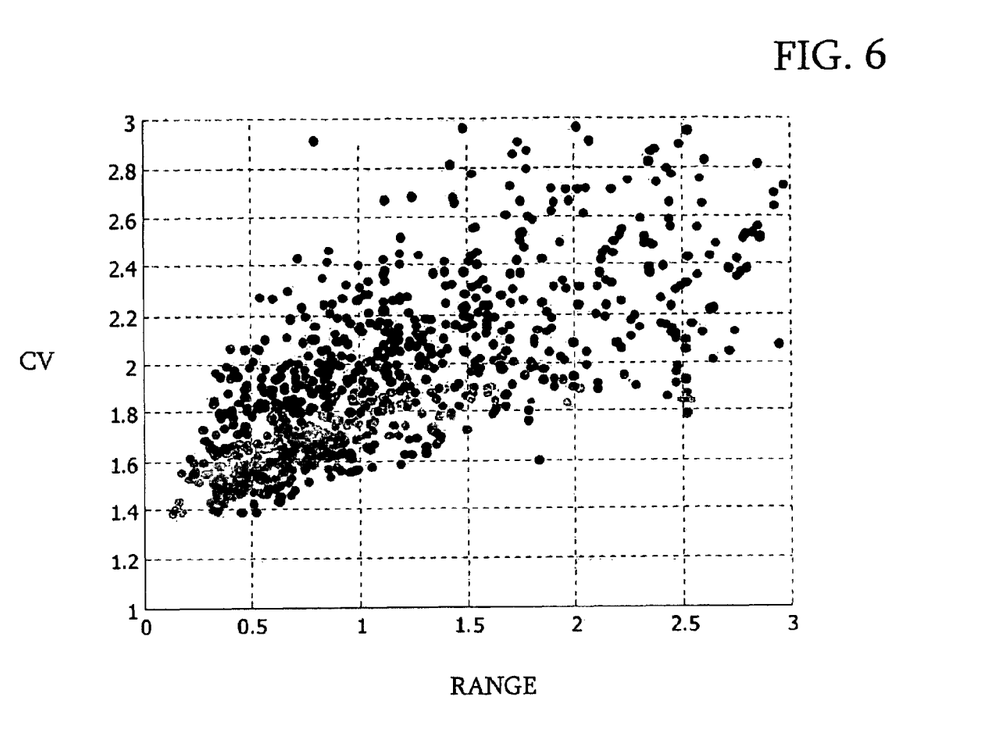
FIG. 6 is a scattergram representing a binary logistic mixed model that incorporates an aggregate of binary responses of observers in a training set, in accordance with a disclosed embodiment of the invention.

Reference is now made to FIG. 6, which is a scattergram representing the logistic mixed model constructed from the collection of physician responses in the training set. It will be noted that the data is more compactly clustered than in either FIG. 4 or FIG. 5.

TABLE 2

| Binary Logistic Mixed Model | | |
| --- | --- | --- |
| Sensitivity | Specificity | Accuracy |
| 80 | 82 | 78 |

Example 2

Figure 7:
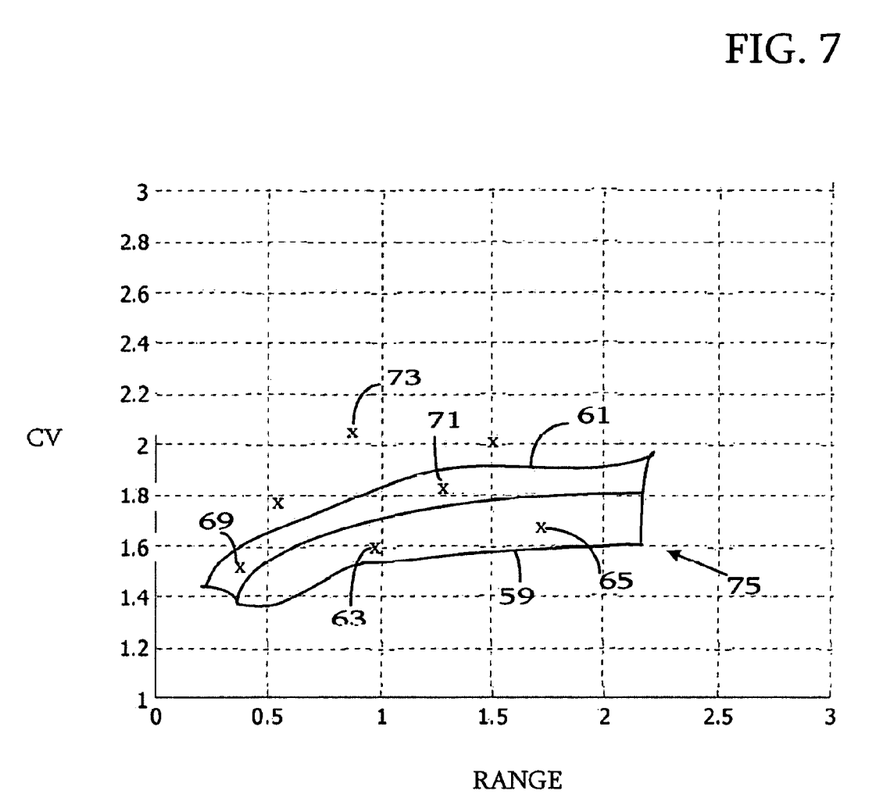
FIG. 7 is a scattergram illustrating the use of a binary logistic mixed model with patient data, in accordance with a disclosed embodiment of the invention.

Reference is now made to FIG. 7, which is a scattergram illustrating the use of a binary logistic mixed model with patient data, in accordance with a disclosed embodiment of the invention. This is a prospective example indicating the application of the binary logistic mixed model shown in FIG. 6 to new patient data. The patient data is to be obtained as described above, and data representing CFAE locations are plotted as "x" symbols. A template 75 is prepared from the scattergram shown in FIG. 6, and outlines a region 59 within which CFAE location data indicate primary ablation sites. CFAE location data lying in a region 61 indicate secondary ablation sites.

In the patient study represented in FIG. 7, the binary logistic mixed model predicts that points 65, 67 represent CFAE locations appropriate for primary ablation. Points 69, 71 represent CFAE locations appropriate for secondary ablation. Points lying outside regions 59, 61, such as point 73, are not considered appropriate for ablation. Typically, a physician initially ablates primary ablation points. Should the results be unsatisfactory, he would proceed to ablate secondary ablation points.

In a series of patient studies, Table 3 presents results from application of the binary logistic mixed model obtained from the training set to the CFAE location data obtained.

TABLE 3

| Binary Logistic Mixed Model | | |
| --- | --- | --- |
| Sensitivity | Specificity | Accuracy |
| 74 | 72 | 72 |

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for locating an arrhythmogenic focus in a heart of a living subject, comprising the steps of:
   obtaining training electrical signal data from respective training locations of a training set of hearts;
   automatically analyzing said training electrical signal data to identify training complex fractionated electrograms therein;
   recording determinations of medical significance of a plurality of observers with respect to said training complex fractionated electrograms;
   generating first estimations of medical significance at said respective training locations by fitting a mixed regression model to said training complex fractionated electrograms and said determinations of medical significance;
   obtaining patient electrical signal data from respective locations of a patient heart;
   automatically analyzing said patient electrical signal data to identify patient complex fractionated electrograms in said patient heart;
   applying said mixed regression model to said patient complex fractionated electrograms to obtain second estimations of medical significance at said respective locations of said patient heart; and
   displaying an indication that one or more of said respective locations of said patient heart are medically significant.

2. The method according to claim 1, wherein said mixed regression model is a binary logistic mixed model having fixed effects and random effects, and wherein said fixed effects comprise a coefficient of variation and a range of said training electrical signal data, and said random effects comprise said first estimations of medical significance.

3. The method according to claim 1, wherein said observers comprise five observers.

4. The method according to claim 1, wherein said determinations of medical significance comprise first decisions to ablate primary ablation locations selected from said respective training locations and second decisions to ablate secondary ablation locations selected from said respective training locations.

5. A computer software product for locating an arrhythmogenic focus in a heart of a living subject, including a computer storage medium in which computer program instructions are stored, which instructions, when executed by a computer, cause the computer to acquire training electrical signal data from respective training locations of a training set of hearts, automatically analyze said training electrical signal data to identify training complex fractionated electrograms therein, record determinations of medical significance of a plurality of observers with respect to said training complex fractionated electrograms, generate first estimations of medical significance at said respective training locations by fitting a mixed regression model to said training complex fractionated electrograms and said determinations of medical significance, obtain patient electrical signal data from respective locations of a patient heart, automatically analyze said patient electrical signal data to identify patient complex fractionated electrograms in said patient heart, apply said mixed regression model to said patient complex fractionated electrograms to obtain second estimations of medical significance at said respective locations of said patient heart, and display an indication that one or more of said respective locations of said patient heart are medically significant.

6. The computer software product according to claim 5, wherein said mixed regression model is a binary logistic mixed model having fixed effects and random effects, and wherein said fixed effects comprise a coefficient of variation and a range of said training electrical signal data, and said random effects comprise said first estimations of medical significance.

7. The computer software product according to claim 5, wherein said determinations of medical significance comprise first decisions to ablate primary ablation locations selected from said respective training locations and second decisions to ablate secondary ablation locations selected from said respective training locations.

8. A medical apparatus for locating an arrhythmogenic focus in a heart of a living subject, comprising:
a memory having programs stored therein; and
a processor connectable to receive an input provided by an intracardiac probe, said processor being coupled to access said memory to execute said programs, wherein said programs cause said processor to acquire training electrical signal data via said probe from respective training locations of a training set of hearts, automatically analyze said training electrical signal data to identify training complex fractionated electrograms therein, record in said memory determinations of medical significance of a plurality of observers with respect to said training complex fractionated electrograms, generate first estimations of medical significance at said respective training locations by fitting a mixed regression model to said training complex fractionated electrograms and said determinations of medical significance, obtain patient electrical signal data via said probe from respective locations of a patient heart, automatically analyze said patient electrical signal data to identify patient complex fractionated electrograms in said patient heart, apply said mixed regression model to said patient complex fractionated electrograms to obtain second estimations of medical significance at said respective locations of said patient heart, and display an indication that one or more of said respective locations of said patient heart are medically significant.

9. The medical apparatus according to claim 8, wherein said mixed regression model is a binary logistic mixed model having fixed effects and random effects, and wherein said fixed effects comprise a coefficient of variation and a range of said training electrical signal data, and said random effects comprise said first estimations of medical significance.

10. The medical apparatus according to claim 8, wherein said determinations of medical significance comprise first decisions to ablate primary ablation locations selected from said respective training locations and second decisions to ablate secondary ablation locations selected from said respective training locations.

* * * * *